United States Patent [19]

Tabacco et al.

[11] Patent Number: 4,703,015

[45] Date of Patent: Oct. 27, 1987

[54] METHOD AND REACTIVE COMPOSITION SUITABLE FOR THE COLORIMETRIC DETERMINATION OF METALS

[75] Inventors: Alessandro Tabacco; Edoardo Moda, both of Siena; Paolo Tarli, Monteriggioni, all of Italy

[73] Assignee: Sclavo, S.p.A., Siena, Italy

[21] Appl. No.: 904,751

[22] Filed: Sep. 5, 1986

Related U.S. Application Data

[63] Continuation of Ser. No. 640,953, Aug. 15, 1984, abandoned.

[30] Foreign Application Priority Data

Sep. 28, 1983 [IT]  Italy ................................ 23028 A/83

[51] Int. Cl.$^4$ ...................... G01N 33/48; G01N 33/52
[52] U.S. Cl. ......................................... 436/74; 436/84; 422/61
[58] Field of Search ........................... 436/74, 84, 910; 422/61; 252/408.1

[56] References Cited

U.S. PATENT DOCUMENTS 4,407,962  10/1983  Tabacco et al. ...................... 436/74

OTHER PUBLICATIONS

Kuban et al, "Comparison of the Reactions of Ferric Ions with Chromazurol S, Eriochromazurol B and Eriochromcyanine R in the Presence of Surface Active Substances . . . ", Collect. Czech. Chem. Commun., 45(10), 2656–69 (1980).
Colour Index, 3rd Ed. (1971) p. 4408.

*Primary Examiner*—S. Leon Bashore
*Assistant Examiner*—Andrew J. Anderson
*Attorney, Agent, or Firm*—Hedman, Gibson, Costigan & Hoare

[57] ABSTRACT

A colorimetric reagent formulation is disclosed for the determination of the ferric iron content of serum. The formulation consists of two aqueous solutions. One solution, acting as chromogenic reagent, consists of a buffer, a soluble salt of an alkali or alkaline earth metal, chromazurol S in acidic form, and either a cationic or nonionic surfactant. The other solution, acting as masking reagent, consists of a complexing agent and if desired the same components of the chromogenic reagent, which are able to prevent the formation of the complex between the chromazurol S, the surfactant and the iron. The complexing agent consists of a polycarboxylic organic acid or salt thereof.

3 Claims, No Drawings

METHOD AND REACTIVE COMPOSITION SUITABLE FOR THE COLORIMETRIC DETERMINATION OF METALS

This is a continuation of application Ser. No. 640,953, filed Aug. 15, 1984, now abandoned.

The present invention relates to a colorimetric reagent which allows the presence to be determined, within different fluids, of metals which can exists in different oxidation states, preferably those which can become trivalent.

The colorimetric reagent, which is the object of the present invention, is particularly suitable to the quantitative determination of metals inside biological fluids and, among others, of the iron in the serum.

The applicants are firmly convinced that the reaction which is disclosed hereinunder, is of general use as concerning the analysis of trivalent metals.

However, because of the great interest in the specific field of the diagnosis of biological fluids, applicants have directed all of the examples of of the present disclosure to the determination of iron in serum.

It will be then easy for those who are skilled in the art, to enlarge the definition of the reagent and the uses of it, always within the purpose and the spirit of the present invention.

The possibility is known of colorimetrically determining the iron (in the serum) by means of the use of various chromogenic complexing agents, or by atomic absorption. The chromogenic complexing agents more largely used are:
Sulphonate batophenanthroline
3-(2-pyridyl)-5,6-bis-(4-phenylsulphonyc acid)
2,4,6-Tripyridyl-s-triazine
2,2'-dipyridyl,
and so on.

According to the methods using these chromogens, the iron in the serum is extracted from transferrin either by deproteination at acidic pH, or by using suitable surfactants.

The iron extracted from transferrin is then reduced to the ferrous state by strong reducers such as sodium dithionite, ascorbic acid, and so on. The reduced iron is then complexed by one of the various chromogenic reagents listed above, forming coloured complexes whose extinction is proportional to the concentration of iron in the original sample. Horiuchi, Y. and Nishida, H. (Jap. Analysis 17 (6) 756, 1968) point out that the chromazurol S (C. I. 43825) in the presence of zephiramine (ammoniumbenzyl-dimethyltetradecyl-chloride) reacts with the Fe(III) to form a coloured chelate having a molar extinction coefficient of about $8.5 \times 10^4$ l.mol$^{-1}$ cm$^{-1}$ at 640 nm. Recently, A. Garčic "Clin. Chim. Acta" 94, 115–119, 1979, has proposed a very sensible chromogen for the determination of ferric iron in the serum, without deproteination. In the method described by the author, Chromazurol B (C. I. 43830) is used in the presence of cetyltrimethyl-ammonium bromide (CTMA).

The molar coefficient of extinction of the Chromazurol B-CTMA-Fe(III/II) complex at 630 nm has been shown to be $1.68 \times 10^5$ l mol$^{-1}$.cm$^{-1}$.

The same author, referring to the works by Horiuchi and Nishida, claims the use of Chromazurol B to be preferable to Chromazurol S, in that the first is more sensible and suffers from less interferences by the other components of the serum.

U.S. Pat. No. 4,407,962 discloses a composition for the colorimetric determination of metals using Chromazurol B. Such a composition results however to be less stable of that using Chromazurol S, indeed, should Chromazurol B be used in the acidic form, ethyl alcohol is to be added (in order to stabilizing the composition).

It has been found that the Chromazurol S (CAS) in the presence of CTMA and under suitable conditions, reacts with iron(III/II) to give an intensely coloured complex with an absorption maximum at 630 nm and with a molar coefficient of extinction of $1.45 \times 10^5$ l mol$^{-1}$.cm$^{-1}$ comparable to that which is obtained under similar conditions with Chromazurol B.

Moreover, the greater solubility of Chromazurol S allows, according to the requirements, not to add the organic solvent, which is used to stabilize the reagent with the Chromazurol B.

Is therefore a first object of the present invention to provide a composition which allows a colorimetric reagent to be formulated, suitable to the determination in the iron of the serum. Such composition consists of two solutions that are, preferably aqueous solutions. One reagent acts as the chromogenic reagent of the iron in the sample, and the other acts as the masking reagent, needed in order to eliminate the interference with the Chromazurol S with proteinic substances present in the serum.

In particular, the chromogenic reagent consists of buffer at acidic pH, an organic and/or inorganic salt of an alkali or alkaline-earth metal, Chromazurol S (as such or salified), a cationic or non ionic surfactant and if desired an additional organic solvent; the masking reagent in turn consists of the same components and contains additionally a complexing agent able to prevent the formation of the complex between the Chromazurol, the surfactant and the iron, such masking reagent containing if desired the complexing agent only.

The various components described hereinabove can be present within the reagent at different concentrations: as for the Chromazurol S, the quantity of it varies within the range of from 0.01 mmoles/liter to 0.3 mmoles/liter; the surfactant, in turn, is added in quantities ranging from 0.1 to 400 times the quantity of Chromazurol. The salt of the alkali or alkalineearth metal, whose function in the case of the analysis of serum is to aid in the extraction of iron from the transferrin, is added to the solution until a satisfactory result is reached, and however in quantities greater than 0.004 moles/liter; the pH varying between 0.4 and 5.6. Finally, in the case of the use of an additional organic solvent, its concentration can vary up to a maximum of 30% relative to the volume of the solution.

As for the masking solution, the complexing agent inhibitor of the complex formation between the Chromazurol, the surfactant and the iron, is added in variable quantities always as a function of its nature and complexing capabilities, and, however, in not lower quantities than Chromazurol.

Among all the possible components, the soluble salt is preferably a salt of magnesium, and, among others, a halogenide; the Chromazurol S, as previously mentioned, can be present as such or salified; the surfactant is chosen among the alkylammonium halogenides, e.g. cetyltrimethylammonium bromide, or among the polyoxyalkylenethers; the complexing agent, present in the masking reagent, is in turn chosen among the polycarboxylic organic acids and their salts, it consists e.g.

of citric acid monohydrate and tribasic sodium citrate bihydrate.

A standard formulation, according to the present invention, is the following:

I. Chromogenic reagent
Buffer acetic acid/KOH pH 4.75 0.5M.
$MgCl_2.6H_2O$ 60 g/liter
CAS 92 mg/liter
CTMA 270 mg/liter.

II. Masking reagent
The concentrations of the various components of the chromogenic reagent remain unchanged in the masking reagent. Are additionally present:
Monohydrate citric acid 5.48 g/liter
Bihydrate tribasic sodium citrate 11,29 g/liter.

The solution, stored away from light at a temperature between 0° C. and 37° C., has a longer stability than one year. The analytical method, based on the use of the formulation according to the present invention, is shown in the reaction scheme here mentioned.

|  | Sample 100/100 cc | Standard | Blank chromogenic reagent | Blank sample | Blank masking reagent |
| --- | --- | --- | --- | --- | --- |
| Serum ml | 0.1 | — | — | 0.1 | — |
| Standard ml | — | 0.1 | — | — | — |
| Distilled water ml | — | — | 0.1 | — | 0.1 |
| Chromogenic reagent I ml | 2.0 | 2.0 | 2.0 | — | — |
| Masking reagent II ml | — | — | — | 2.0 | 2.0 |

Incubation for 20 minutes at 37° C. and reading at 640 nm.

A further object of the present invention is a method using the aforeshown composition for the determination of iron in biological fluids comprising the following stages:

(i) addition of the chromogenic reagent to the biological fluid;
(ii) incubation at a temperature varying between 0° C. and 50° C.;
(iii) reading of the optical density at a determined wave length against a solution of "blank chromogenic reagent".

If in the biological fluid interfering substances are present, such as e.g., β-lipoproteins, the following operations are instead carried out:

(i) addition of the chromogenic fluid to the biological fluid;
(ii) incubation at a temperature comprised between 0° C. and 50° C.;
(iii) reading of the optical density at a determined wave length against a solution of "blank chromogenic reagent";
(iv) addition of a complexing agent to the biological fluid containing the colorimetric reagent, such complexing agent being capable of inhibiting the formation of the complex, or addition to the biological fluid of the masking reagent containing a complexing agent together with the same components of the colorimetric reagent.
(v) incubation at a temperature comprised between 0° C. and 50° C.;
(vi) reading of the optical density, at the same wave length as shown at the paragraph (iii), against a solution of a "blank masking reagent" and subtraction of the value of the optical density due to the interfering substances from the value obtained with the biological fluid and the chromogenic reactive reagent.

EXAMPLE 1

Using a composition having the standard formulation above shown, a series of tests have been carried out, in order to verify the characteristics of the same.

1. Accuracy

Adding graduated and known quantities of $Fe^{+3}$ to a serum, an average recovery has been obtained of 98.5%, linear between 0 and 100 μg/100 ml of added iron. This means that the iron in the serum has been slightly underdosed, but with a negligible error, as a matter of fact the correlation coefficient of the quantity of added iron to the quantity of measured iron was 0.999.

2. Linearity

The correlation of the extinction at 640 nm and the concentration of iron has resulted to be linear up to 600 μg/100 ml of iron in the sample.

3. Comparison

The reagent of the invention, compared to the method described by Tabacco et al. (Clin. Chim. Acta, 114, 287, 1981) which uses as the chromogen the Chromazurol B, gave the following result on 32 samples of human serum: comparison $y=1.07.\times+14.5$ μg/dl, with r (correlation coefficient=0.96).

4. Interferences

The interferences have been tested of bivalent and trivalent ions normally present, or which can be present in pathological conditions in human blood.

At the concentrations of ions in the sample (μmole/liter) hereunder shown, the percentage variations of the initial value of the iron in the sample were negligible: $Ca^{2+}=5.000$; $Cu^{2+}=80$; $Pb^{2+}=25$; $Al^{3+}10$; $Zn=80$.

We claim:

1. Method for the determination of iron in biological fluids which comprises the following steps:
   (i) adding to a biological fluid a colorimetric reagent consisting of a buffer at acidic pH, an organic and/or inorganic salt of an alkali or alkaline earth metal, Chromazurol S in acidic form and a cationic or non ionic surfactant;
   (ii) incubating the product of (i) at a temperature variable between 0° C. and 50° C.; and
   (iii) reading the optical density at a determined wave length against a solution of a blank chromogenic reagent.

2. Method for the determination of iron in a biological fluid in which interfering substances are present, said method comprising the following steps:
   (i) adding to the biological fluid a colorimetric reagent consisting of a buffer at acidic pH, an inorganic and/or organic salt of an alkali or alkaline earth metal, Chromazurol S in acidic form and a cationic or non ionic surfactant;
   (ii) incubating the product of (i) at a temperature within the range of from 0° C. and 50° C.;
   (iii) reading the optical density of the product of step (ii);

(iv) adding to the biological fluid containing the colorimetric reagent, a complexing agent able to inhibit the formation of a complex, between the Chromazurol S, the surfactant and the iron, or in the alternative adding to the biological fluid a masking reagent containing a complexing agent together with the same components of the colorimetric reagent;

(v) incubating the product of (iv) at a temperature within the range of from 0° C. to 50° C.; and (vi) reading the optical density of the product of step (v) at the same wave length as shown in step (iii), against a solution of a blank masking reagent and subtracting the value of the optical density due to the interfering substances of the product of step (v) from the value obtained with the biological fluid and chromogenic reagent of the product of step (ii).

3. A kit for the determination of serum iron, said kit comprising a colorimetric reagent suitable to the determination of iron in biological fluids, said reagent consisting of two solutions, in which the first solution consists of a buffer at an acidic pH, a magnesium halogenide, Chromazuraol S in acidic form, and cetyltrimethyl ammonium bromide, the second solution containing a complexing agent able to inhibit the formation of a complex between Chromazurol S in acidic form, the cetyltrimethylam-monium bromide and the iron, alone or with the other components of the first solution.

* * * * *